United States Patent [19]

Vige et al.

[11] Patent Number: 6,043,280
[45] Date of Patent: Mar. 28, 2000

[54] USE OF BENZONAPHTHALENE DERIVATIVES TO MAKE MEDICAMENTS FOR TREATING DISEASES OF THE CENTRAL NERVOUS SYSTEM

[75] Inventors: Xavier Vige, Longjumeau; Jésus Benavides, Châtenay-Malabry; Braham Shroot, Antibes; Véronique Taupin, Paris, all of France

[73] Assignee: Galderma Research & Development, S.N.C., Valbonne, France

[21] Appl. No.: 09/155,598

[22] PCT Filed: Apr. 2, 1997

[86] PCT No.: PCT/FR97/00590

§ 371 Date: Jan. 8, 1999

§ 102(e) Date: Jan. 8, 1999

[87] PCT Pub. No.: WO97/37648

PCT Pub. Date: Oct. 16, 1997

[30] Foreign Application Priority Data

Apr. 5, 1996 [FR] France ................................. 96 04359

[51] Int. Cl.[7] ........................ A61K 31/19; A61K 31/235; A61K 31/165

[52] U.S. Cl. ........................ 514/569; 514/532; 514/544; 514/617

[58] Field of Search ..................................... 514/569, 617, 514/532, 544

[56] References Cited

U.S. PATENT DOCUMENTS 5,455,248  10/1995  Dehaven-Hudkins .

OTHER PUBLICATIONS

Database Medline, US National Library of Medicine (NLM), Bethesda, MD, an: 96178020, Shalita A. et al, "A comparison of the efficacy and safety of adapalene gel 0.1% and treatment gel 0.0025 % in the treatment of acne vulgaris: a multicenter trial" XP002035679 & J M Acad Dermatol, vol. 34, No. 3, Mar. 1996, pp. 482–485.

*Primary Examiner*—William R. A. Jarvis
*Attorney, Agent, or Firm*—Burns, Doane, Swecker & Mathis, L.L.P.

[57] ABSTRACT

This invention relates to the use of benzonaphthalene compounds for the treatment of peripheral neuropathies, central neurodegenerative diseases and autoimmune diseases of the nervous system.

4 Claims, No Drawings

USE OF BENZONAPHTHALENE DERIVATIVES TO MAKE MEDICAMENTS FOR TREATING DISEASES OF THE CENTRAL NERVOUS SYSTEM

This application is a 371 of PCT/FR97/00590, filed Apr. 2, 1997.

The present invention relates to the use of the compounds corresponding to the formula (I) given below and of their salts, for the manufacture of medicaments for the treatment of peripheral neuropathies, central neurodegenerative diseases and autoimmune diseases of the nervous system.

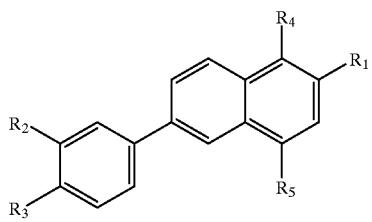

these compounds being described, along with their method of preparation, in Patent EP 0,199,636. In formula (I):

$R_1$ represents a group $—COR_6$ or $CH_2OH$, $R_6$ representing a radical

or a radical $OR_7$, $R_7$ representing a hydrogen atom, an alkyl radical having from 1 to 20 carbon atoms, a monohydroxyalkyl radical, or a polyhydroxyalkyl radical, r' and r" representing a hydrogen atom, a lower alkyl radical, a mono- or polyhydroxyalkyl radical, an optionally substituted aryl radical or an amino acid or amino sugar residue or alternatively taken together form a heterocycle, $R_2$ represents a hydrogen atom, a branched or unbranched alkyl radical having from 1 to 15 carbon atoms, an alkoxy radical having from 1 to 4 carbon atoms, or a cycloaliphatic radical, $R_3$ represents a hydrogen atom, a hydroxyl radical, a branched or unbranched alkyl radical having from 1 to 4 carbon atoms, an alkoxy radical having from 1 to 10 carbon atoms, a substituted or unsubstituted cycloaliphatic radical, a thiocycloaliphatic radical or a radical of formula $—O—Si(CH_3)_2—R_8$, $R_8$ representing a linear or branched lower alkyl radical, $R_4$ and $R_5$, which are identical or different, represent a hydrogen atom, a lower alkyl radical, a hydroxyl radical or a lower acyloxy radical.

According to the present invention, among the branched or unbranched alkyl radicals having from 1 to 20 carbon atoms or from 1 to 15 carbon atoms, there may be advantageously mentioned the methyl, ethyl, isopropyl, butyl, tert-butyl, hexyl, octyl, nonyl, 2-ethylhexyl and dodecyl radicals. Preferably, these radicals have from 1 to 12 carbon atoms.

When it is a lower radical, the alkyl radical generally comprises from 1 to 6 carbon atoms. There may be mentioned, as lower alkyl radical, the methyl, ethyl, propyl, isopropyl, butyl, tert-butyl and hexyl radicals.

Monohydroxyalkyl or polyhydroxyalkyl radical should be understood to mean a radical containing from 1 to 6 carbon atoms and from 1 to 5 hydroxyl groups.

Among the monohydroxyalkyl radicals, a radical preferably containing 1 or 3 carbon atoms, in particular the hydroxymethyl, 2-hydroxyethyl and 2- or 3-hydroxypropyl radicals, is preferred.

Among the polyhydroxyalkyl radicals, a radical having from 3 to 6 carbon atoms and from 2 to 5 hydroxyl groups, such as the 2,3-dihydroxypropyl, 2,3,4-trihydroxybutyl and 2,3,4,5-tetrahydroxypentyl radicals or the pentaerythritol residue, is preferred.

Among the aryl radicals, a phenyl, thiophene or pyridine radical, optionally substituted with at least one hydrogen atom, a hydroxyl radical, an alkyl radical, a nitro functional group, a methoxy group or an optionally substituted amine functional group, is preferred. The optionally substituted phenyl radical is preferred.

Amino acid residue is understood to mean in particular a residue derived from one of the amino acids such as lysine, glycine or aspartic acid, and peptide residue is understood to mean more particularly a dipeptide or tripeptide residue resulting from the combination of amino acids.

Among the amino sugar residues, there may be mentioned the residues derived from glucosamine, galactosamine and mannosamine.

Heterocycle is preferably understood to mean a piperidino, morpholino, pyrrolidino or piperazino radical, optionally substituted at the 4-position with a $C_1$–$C_6$ alkyl or polyhydroxyalkyl radical as defined above.

Among the alkoxy radicals having from 1 to 10 carbon atoms, there may be mentioned in particular the methoxy, ethoxy, isopropoxy, hexyloxy and decyloxy radical.

Among the lower acyloxy radicals, there are understood radicals having from 1 to 4 carbon atoms, such as for example the acetyloxy or propionyloxy radicals.

Cycloaliphatic radical is understood to mean a cyclic or polycyclic alkane radical containing from 1 to 10 carbon atoms, optionally substituted with one or more halogen atoms or one or more hydroxyl radicals. There may be mentioned in particular the adamantyl or 1-methylcyclohexyl radicals.

The preferred thiocycloaliphatic radical is the 1-adamantylthio radical.

Among the halogen atoms, fluorine or chlorine is preferred.

The compounds (I) have been studied in several tests for measuring neurotrophic activity.

Effects of the compounds on the production of NGF by astrocytes in culture

The primary astrocyte cultures are prepared from the cerebral cortex of 1- to 2-day old newborn rats. After dissection, the cortices are broken up mechanically by passing through a Blutex nylon (83 mM mesh). The cells are cultured in a DMEM/F12 medium (Gibco, Brl 1:1) containing 10% foetal calf serum, 2.5 mM L-glutamine, 100 U/ml of penicillin and 100 mg/ml of streptomycin (1 cortex per 30 ml) in 12-well Corning plates in an amount of 1 ml of cellular preparation per well. The plates are placed at 37° C. in an incubator saturated with 5% $CO_2$, the medium is replaced every three days and the cultures are used on the 7th day of culture (80–90% confluence). The treatments with the different compounds are then carried out with 500 ml per well of medium which is described above, for 40 h. At the end of the treatment, the NGF secreted into the medium is assayed by immunoenzymatic assay and the membrane protein level is evaluated by the Bradford technique using Coomassie blue.

Assay of NGF

The NGF levels are evaluated by an immunoenzymatic technique. 96-well plates are treated for 2 h at 37° C. with an anti-NGF monoclonal antibody (0.67 mg/ml) solubilized in 50 μm $Na_2CO_3$ buffer at pH 9.6. The emptied plates are then incubated for 1 h at room temperature with 1% bovine serum albumin solubilized in the same buffer, and washed with a 50 mM Tris-HCl buffer (pH 7.0) containing 200 mM NaCl, 10 mM $CaCl_2$, 0.1% Triton X-100 and 0.0504 $NaN_3$ (Buffer A). The astrocyte medium diluted ⁹⁄₁₀ in an extraction buffer (50 mM Tris-HCl, pH 7, 200 mM NaCl, 1% BSA, 0.1% Triton X-100, 4 mg/ml aprotinin, 2 mM EDTA, 0.1 mM benzethonium chloride and 0.05% $NaN_3$) and the NGF standards (series from 10 to 320 pg/ml) are then added in duplicate (0.1 ml/well). The plates are incubated for about 16 h at 4° C. After washing with the buffer A, the plates are incubated for 4 h at 37° C. with a second anti-NGF monoclonal antibody coupled to β-galactosidase (0.13–0.15 U/ml). After washing with the buffer A, the plates are incubated for 2 to 3 h at 37° C. with the β-galactosidase substrate, chlorophenol red-β-D-galactopyranoside (2 mg/ml), prepared in 10 mM EEPES (pH 7.0) containing 150 mM NaCl, 2 mM $MgCl_2$, 0.1% $NaN_3$ and 1% BSA. The reaction product is measured at 570 nM by a Bio Kinetics Reader EL 340.

Results

The compounds of the invention increase the production of NGF. At the concentration of 100 nM, the most active compounds of the invention increase the production of NGF up to more than 70% compared with the controls.

Effects of the compounds on neuritogenesis and the neuritic growth of the dorsal root ganglia The dorsal root ganglia (DRG) are removed from 14-day old rat foetuses. The samples are collected at 3 different levels of the marrow (cervical, thoracic and sacral). The DRGs are cultured for 24 h in a DMEM medium (Gibco, Brl) containing 5% foetal calf serum, 100 U/ml of penicillin and 100 μg/ml of streptomycin, with or without the compound to be studied in an incubator saturated with 5% $CO_2$. The medium is then replaced with an identical medium lacking foetal calf serum and containing 1 μM cytosine arabinoside (SIGMA) to inhibit the proliferation of the non-neuronal cells.

The effects of the compounds on neuritogenesis and neuritic growth are evaluated 48 h after placing in culture by a morphometric technique using a BIOCOM image analysis system.

Results

Several compounds of the invention increase the neuritogenesis of explants of dorsal root ganglia by more than 100% compared with the controls, at the concentration of 100 nM.

The therapeutic potential of the compounds of the invention for the treatment of autoimmune diseases of the nervous system was also evaluated.

Effects of the compounds on the proliferation of mouse lymphocytes having an experimental autoimmune encephalitis (EAE)

Induction of the EAE:

Female SJL/J mice are injected subcutaneously, on D0 and D7, with myelin basic protein (MBP, 400 μg/mouse) emulsified in complete Freund's adjuvant. About 20 days after the first immunization, the lymph nodes of the animals which develop clinical signs of EAE are used for the test of proliferation.

Measurement of the proliferation of the lymphocytes:

The ganglia are removed and broken up mechanically by passage through a metal sieve. The cells are cultured in an RPMI medium (Gibco, BRL) containing 10% decomplementized foetal calf serum, 2.5 mM L-glutamine, 100 U/ml of penicillin, 100 μg/ml of streptomycin and 0.5% 2-mercaptoethanol in an amount of 250,000 cells per well in TPP 96-well plates. The plates are placed at 37° C. in an incubator saturated with 5% $CO_2$. The cells are treated on the day of the culture with the different analogues of retinoic acid in the absence or in the presence of MBP (25 μg/ml; antigenic stimulation) for 96 h. The proliferation is evaluated by measuring the incorporation of tritiated thymidine added to the culture medium during the last 16 hours of incubation.

Results

The analysis of the results shows that the compounds of the invention inhibit the proliferation of the lymphocytes obtained from EAE mice with $IC_{50}$ values ranging from 0.1 to 100 nM.

Effects of the compounds on the production of TNF-α (tumour necrosis factor-α) by activated microglial cells Primary cultures of microglial cells:

The microglial cells are prepared from cortices of 1-day old newborn rats. The cells are cultured in a DMEM medium (Gibco, BRL) containing 10% foetal calf serum (inactivated myoclone), 2.5 mM L-glutamine, 4.5 g/l of L-glucose and 100 μg/ml of gentamycin in TPP 96-well plates. The cells are treated with the different analogues of retinoic acid and stimulated with 1 μg/ml of lipopolysaccharide (LPS) in order to induce the production of TNFα. After 18 h of incubation, the culture media are collected for the assay of TNFα.

Assay of TNFα:

The TNFα levels in the microglial cell culture supernatants are determined using a test of cytotoxicity on the cell line L929. The test is visualized by means of the colorimetric assay of MTT.

Results

The compounds of the invention decrease the production of TNFα by activated microglial cells in culture, with effects ranging up to 50% decrease at the concentration of 10 nM.

The results show that the compounds of the invention have a neurotrophic activity which may find application in the treatment of peripheral neuropathies of the trauma, ischaemic, metabolic, infectious, alcoholic, iatrogenic or genetic type, and in the treatment of diseases affecting the motoneurons, such as amyotrophic lateral sclerosis and spinal amyotrophies. They may also be used for the preparation of medicaments for the treatment of retinopathies, cerebral senility, dementia following multiple infarctions, vascular dementia, in the treatment of olivopontocerebellar atrophy and other neurodegenerative diseases, for example Alzheimer's disease, Pick's disease or Huntington's chorea. The compounds of the invention may also find application in the prevention of neuronal death following a cerebrovascular accident or a medullary or cranial trauma.

They may also prove active in pathologies of autoimmune origin such as multiple sclerosis, Guillain-Barré's disease and myasthenia gravis.

The most active compounds correspond to the following formula

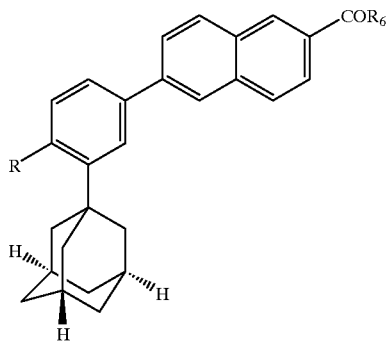

in which $R_6$ represents a radical

or a radical $OR_7$, $R_7$ representing a hydrogen atom, an alkyl radical having from 1 to 20 carbon atoms, a monohydroxyalkyl radical or a polyhydroxyalkyl radical, r' and r" representing a hydrogen atom, a lower alkyl radical, a mono- or polyhydroxyalkyl radical, an optionally substituted aryl radical or an amino acid or amino sugar residue or taken together form a heterocycle, R represents a hydrogen atom, a hydroxyl radical, a branched or unbranched alkyl radical having from 1 to 4 carbon atoms or an alkoxy radical of 1 to 4 carbon atoms.

The 6-[3-(1-adamantyl)-4-methoxyphenyl]-2-naphthoic and 6-[3-(1-adamantyl)-4-hydroxyphenyl]-2-naphthoic acids, their esters (in particular their methyl esters) and their amides are the preferred compounds.

The compounds may be used in combination with one or more compounds of the following classes: steroidal or nonsteroidal anti-inflammatory agents, antiviral agents (in particular antiherpes), immunosuppressants and immunomodulatory agents.

The compounds may be provided in any pharmaceutical forms suitable for enteral, parenteral or local administration, in combination with appropriate excipients, for example in the form of tablets, sugar-coated tablets, gelatin capsules, capsules, suppositories, patches, oral or injectable solutions or suspensions. The daily administration may vary from 0.01 to 100 mg of active ingredient.

We claim:

1. A method for the prevention or treatment of peripheral neuropathies, central neurodegenerative diseases or autoimmune diseases of the central nervous system, said method comprising administering an effective amount of a compound corresponding to the formula (I) and of their salts,

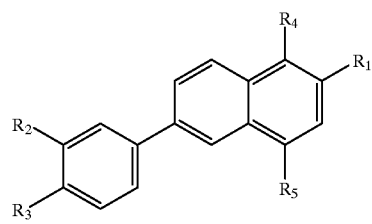

in which $R_1$ represents a group —$COR_6$ or $CH_2OH$, $R_6$ representing a radical

or a radical $OR_7$, $R_7$ representing a hydrogen atom, an alkyl radical having from 1 to 20 carbon atoms, a monohydroxyalkyl radical, or a polyhydroxyalkyl radical, r' and r" representing a hydrogen atom, a lower allyl radical, a mono- or polyhydroxyalkyl radical, an optionally substituted aryl radical or an amino acid or amino sugar residue or alternatively taken together form a heterocycle, $R_2$ represents a hydrogen atom, a branched or unbranched alkyl radical having from 1 to 15 carbon atoms, an alkoxy radical having from 1 to 4 carbon atoms, or a cycloaliphatic radical, $R_3$ represents a hydrogen atom, a hydroxyl radical, a branched or unbranched alkyl radical having from 1 to 4 carbon atoms, an alkoxy radical having from 1 to 10 carbon atoms, a substituted or unsubstituted cycloaliphatic radical, a thiocycloaliphatic radical or a radical of formula —O—Si($CH_3$)$_2$—$R_8$, $R_8$ representing a linear or branched lower alkyl radical, $R_4$ and $R_5$, which are identical or different, represent a hydrogen atom, a lower alkyl radical, a hydroxyl radical or a lower acyloxy radical, to a human or animal in need of such prevention or treatment.

2. A method for the prevention or treatment of peripheral neuropathies, central neurodegenerative diseases or autoimmune diseases of the central nervous system, said method comprising administering an effective amount of a compound corresponding to the formula

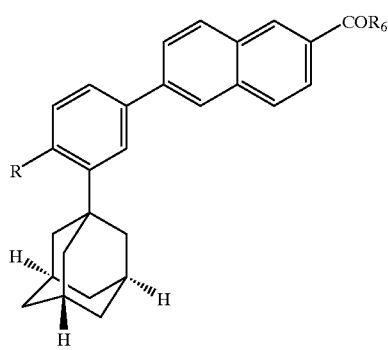

in which

R₆ represents a radical or a radical OR₇, R₇ representing a hydrogen atom, an alkyl radical having from 1 to 20 carbon atoms, a monohydroxyalkyl radical, or a polyhydroxyalkyl radical, r' and r" representing a hydrogen atom, a lower alkyl radical, a mono- or polyhydroxyalkyl radical, an optionally substituted aryl radical or an amino acid or amino sugar residue or taken together form a heterocycle, R represents a hydrogen atom, a hydroxyl radical, a branched or unbranched alkyl radical having from 1 to 4 carbon atoms or an alkoxy radical of 1 to 4 carbon atoms to a human or animal in need of such prevention or treatment.

3. A method for the prevention or treatment of peripheral neuropathies, central neurodegenerative diseases or autoimmune diseases of the central nervous system, said method comprising administering an effective amount of 6-[3-(1-adamantyl)4-methoxyphenyl]-2-naphthoic acid or ester or amide thereof to a human or animal in need of such prevention or treatment.

4. A method for the prevention or treatment of peripheral neuropathies, central neurodegenerative diseases or autoimnmune diseases of the central nervous system, said method comprising administering an effective amount of 6-[3-(1-adamantyl)4-hydroxyphenyl]-2-naphthoic acid or ester or amide thereof to a human or animal in need of such prevention or treatment.

* * * * *